United States Patent
Franck (10) Patent No.: US 11,147,517 B2
(45) Date of Patent: Oct. 19, 2021

(54) PHYSIOLOGICAL MEASUREMENT DEVICE WITH COMMON MODE INTERFERENCE SUPPRESSION

(71) Applicant: KONINKLIJKE PHILIPS N.V., Eindhoven (NL)

(72) Inventor: Christoph Florian Franck, Magstadt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 92 days.

(21) Appl. No.: 16/490,637

(22) PCT Filed: Mar. 5, 2018

(86) PCT No.: PCT/EP2018/055239
§ 371 (c)(1),
(2) Date: Sep. 3, 2019

(87) PCT Pub. No.: WO2018/162365
PCT Pub. Date: Sep. 13, 2018

(65) Prior Publication Data
US 2020/0000411 A1    Jan. 2, 2020

(30) Foreign Application Priority Data
Mar. 7, 2017  (EP) .................................. 17159656

(51) Int. Cl.
*A61B 5/00*       (2006.01)
*A61B 5/318*     (2021.01)

(52) U.S. Cl.
CPC ............ *A61B 5/7203* (2013.01); *A61B 5/318* (2021.01); *A61B 5/725* (2013.01)

(58) Field of Classification Search
CPC .............. A61B 5/305; A61B 5/30–398; A61B 5/72–7217; A61B 5/725
See application file for complete search history.

(56) References Cited

U.S. PATENT DOCUMENTS

| 5,421,342 A * | 6/1995 | Mortara .................... A61B 5/30 |
| | | 600/508 |
| 6,377,845 B1 | 4/2002 | Kinast |

(Continued)

FOREIGN PATENT DOCUMENTS

| WO | 2004084087 A1 | 9/2004 |
| WO | 2013138372 A1 | 9/2013 |
| WO | 2016162497 A1 | 10/2016 |

OTHER PUBLICATIONS

International Search Report and Written Opinion, International Application No. PCT/EP2018/055239, dated Jun. 15, 2018.

(Continued)

*Primary Examiner* — Scott M. Getzow (57) ABSTRACT

The described embodiments relate to systems, methods, and apparatuses for reducing interference of signals transmitted by a physiological measurement device (108, 210, 312), such as an electrocardiogram device. The physiological measurement device can employ filters (308) that use coefficients to reduce time-domain differences between response signals of the physiological measurement device. The coefficients can be derived during a calibration process where each channel of the physiological measurement device is supplied a test signal (202) for identifying the channel with the slowest or most delayed response. Thereafter, when a monitor signal is compiled from response signals filtered using the coefficients, differences in timing between the response signals will not result in distortion of the monitor signal, thereby rendering the monitor signal more accurate for measurement purposes.

9 Claims, 5 Drawing Sheets

(56) References Cited

U.S. PATENT DOCUMENTS

| | | |
|---|---|---|
| 2005/0234329 A1 | 10/2005 | Kraus, Jr. et al. |
| 2011/0319777 A1 | 12/2011 | Mehrotra et al. |
| 2012/0046706 A1* | 2/2012 | Anderson ............ G06K 9/0053 607/5 |
| 2014/0222382 A1* | 8/2014 | Patel ........................ A61B 5/24 702/191 |

OTHER PUBLICATIONS

Bekkeng, J., "Signal sampling", Lecture Notes, Jan. 2017.

Abächerli, R. et al., "Suppression of MR gradient artefacts on electrophysiological signals based on an adaptive real-time filter with LMS coefficient updates", Magnetic Resonance Materials in Physics, Biology and Medicine, Mar. 2005, vol. 18, Issue 1, pp. 41-50.

* cited by examiner

PHYSIOLOGICAL MEASUREMENT DEVICE WITH COMMON MODE INTERFERENCE SUPPRESSION

CROSS-REFERENCE TO PRIOR APPLICATIONS

This application is the U.S. National Phase application under 35 U.S.C. § 371 of International Application No. PCT/EP2018/055239, filed on 5 Mar. 2018, which claims the benefit of European Patent Application No. 17159656.2, filed on 7 Mar. 2017. These applications are hereby incorporated by reference herein.

FIELD OF THE INVENTION

The present disclosure is directed generally to physiological measurement devices. More particularly, but not exclusively, the described embodiments relate to systems, methods, and apparatuses for mitigating common mode interference using filters adapted for individual channels of a physiological measurement device, such as an electrocardiogram device.

BACKGROUND OF THE INVENTION

Conducting physiological measurements can prove difficult because of the sensitivity of many bodily functions and the lack of intuitive means for conducting such measurements. For example, during an electrocardiogram, multiple low voltage signals are applied to the body in order to capture polarity changes in organs, such as the heart. Low voltage signals are often used because cells in the body typically only generate intrinsically small voltages. Low voltage signals can be susceptible to interference from sources internal and external to the body, and the interference can result in artifacts appearing in signals generated during the electrocardiogram.

US 2011/0319777 A1 describes a device and method for filtering impulsive noise and channel switching noise at analog-to-digital converters (ADC) in an electrocardiograph (ECG) device with multiplexed electronic signal channels (ESCs). The filtering is based on an implementation of Burst Sampling technique. Real time digital FIR filters are used for removing other types of noise in ECG signals. The ECG device includes features of self-calibration, clip detection and drawing of power from a USB port of a PC, batteries or an external power source. The ECG monitoring device measures real time ECG signals with automated data recording, data storage and retrieval, data transmission/transfer to an external system, along with parameter extraction for ECG analysis.

WO 2013/138372 A1 describes a mobile system for analyzing ECG data that includes an analog front end module coupled to a mobile consumer device. The analog front end module is configured to collect ECG data from one or more leads and is operable to convert the analog ECG data to digital ECG data. The mobile consumer device, such as a smart phone, is coupled to receive the digital ECG data, and is configured to perform QRS detection using a filter whose cutoff frequency is adapted to a noise level in real time. The ECG signal is amplified non-linearly and three windowed threshold signals are derived. The cutoff frequency for the QRS detection is dynamically selected as a function of the threshold signals. A sample in the amplified signal is identified to be a heartbeat point only when the sample value is equal to the first threshold signal and greater than the filtered threshold signal.

SUMMARY OF THE INVENTION

The present disclosure is directed to systems, methods, and apparatuses for removing common mode interference occurring at a physiological measurement device. In some embodiments, a method is set forth for minimizing common mode interference at a physiological measurement system having input channels and analog circuitry electrically coupled to electrodes for measuring an electrophysiological signal. The method can include steps of receiving analog test signals at the input channels, generating response signals at the analog circuitry in response to receiving the analog test signals, converting each response signal into digital data samples, and storing, in the memory, the digital data samples in association with each of the input channels. The steps can further include analyzing the digital data samples for each of the input channels to determine a reference input channel, determining a set of digital filter coefficients for each input channel other than the reference input channel, and applying a filter to each input channel during operation of said physiological measurement system. Each filter can operate according to a digital filter coefficient from the set of digital filter coefficients to minimize time-domain differences between the reference input channel and each input channel other than the reference input channel. The analog test signals can include a square wave that is superimposed with a sine wave. Furthermore, converting each response signal into digital samples can include sampling at least one response signal at a rate that is greater than a frequency of the sine wave. In some embodiments, the square wave can have a frequency that is less than a bandwidth of the physiological measurement system. Additionally, the set of digital filter coefficients can be calculated according to a least squares error estimation. Analyzing the digital data samples for each of the input channels to determine the reference input channel can include identifying a response signal that has the last zero crossing. Moreover, analyzing the digital data samples for each of the input channels to determine the reference input channel can include identifying a response signal that has the slowest slew rate. In some embodiments, the filter at each input channel is a finite impulse response filter. The set of digital filter coefficients can include at least 2 coefficients. Furthermore, converting each response signal into digital data samples can be performed using sequential data sampling with an analog to digital converter and a multiplexer that is connected between the analog to digital converter and the analog circuitry. The sequential data sampling can be performed at least at 32000 samples per second.

In other embodiments, a physiological measurement device is set forth. The physiological measurement device can include input channels comprising electrodes that are configured to receive physiological measurement signals and analog circuitry connected to the input channels and configured to receive the physiological measurement signals and, in response, output response signals. The physiological measurement device can also include an analog to digital converter connected to the analog circuitry and configured to convert one or more response signals into digital samples, and one or more filters connected to the analog to digital converter and configured to filter the digital samples. Each of the one or more filters operates according to a coefficient for minimizing time-domain differences between the response signals. In some embodiment, the physiological measurement device can include a signal processor configured to provide a differential signal based on a difference between filtered digital samples of at least two different response signals. Each of the one or more filters can be assigned to an input channel of the input channels, and the coefficient for each filter can be based on a calibration of the input channel. The one or more filters can operate to conform the digital samples to be more similar to a response signal corresponding to a predetermined input channel of the input channels.

A further aspect of the present invention is a system for performing a calibration of a physiological measurement device, herein also referred to as calibrating system, in order to generate coefficients for filters that can be applied during operation of the physiological measurement device. The system comprises an analysis unit configured to analyze digital data samples for each of the input channels of the physiological measurement device, to determine a reference input channel. It also comprises a coefficient determining unit, for instance in the form of a coefficient generator, that is configured to determine a set of digital filter coefficients for each input channel other than the reference input channel. The filter coefficients are output by the coefficient determining unit to the physiological measurement device for use in its one or more filters used to filter the digital samples, wherein each of the one or more filters operates according to one or more digital filter coefficients of the set of digital filter coefficients for minimizing time-domain differences between the response signals, in particular between the reference input channel and each input channel other than the reference input channel.

The calibrating system can be embodied as software or hardware or a combination of hardware and software on one or more devices that are capable of interacting with a physiological measurement device. The calibrating system can thus be provided as an add-on module to a physiological measurement device or system.

The term "controller" is used herein generally to describe various apparatus relating to the operation of one or more devices and/or components. A controller can be implemented in numerous ways (e.g., such as with dedicated hardware) to perform various functions discussed herein. A "processor" is one example of a controller, which employs one or more microprocessors that may be programmed using software (e.g., machine code to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and nonvolatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or machine code) that can be employed to program one or more processors or controllers.

In one network implementation, one or more devices coupled to a network may serve as a controller for one or more other devices coupled to the network (e.g., in a master/slave relationship). In another implementation, a networked environment may include one or more dedicated controllers that are configured to control one or more of the devices coupled to the network. Generally, multiple devices coupled to the network each may have access to data that is present on the communications medium or media; however, a given device may be "addressable" in that it is configured to selectively exchange data with (i.e., receive data from and/or transmit data to) the network, based, for example, on one or more particular identifiers (e.g., "addresses") assigned to it.

The term "network" as used herein refers to any interconnection of two or more devices (including controllers or processors) that facilitates the transport of information (e.g., for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, a mouse, keyboard, keypad, various types of game controllers (e.g., joysticks), track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

An electrocardiogram (ECG) is a technology used to monitor medical conditions of a person to identify and evaluate abnormalities. Such medical conditions can include cardiac rhythm, which is a function of electrical signals that cause a person's heart to periodically relax and contract. The ECG can monitor cardiac rhythm by measuring changes of the heart that are exhibited when the heart is beating. The polarity changes can be measured using electrodes that can be attached to various locations on a person's body. The locations can be selected in order to obtain measurements of voltage at different directions relative to the direction of the electrical signals that are causing the cardiac rhythm. Voltage differences measured between electrodes can be indicative of physiological signals that operate to control the body. This voltage difference can be referred to as an ECG vector, which can contain information about the magnitude of the voltage as well as its direction. The ECG vector can be a weighted sum of electrode voltages where the sum of all weighted values is zero and at least two weighed values are not zero. For example, electrode_X-electrode_Y and electrode_X-0.5*electrode_Y-0.5*electrode_Z are examples of ECG vectors, while electrode_X-0.5*electrode_Y is not due to the sum of the weighting values being different from zero.

The accuracy of such measurements can depend on the selected locations of the electrodes, as well as the quality of the signals being transmitted through the electrodes and their respective wires. In an ideal case, calculation of voltage differences would eliminate any signal components that affect all electrodes equally (i.e., common mode interference). However, if the amount of interference is too large compared to the signal, an overall pattern of electrical activity measured at the body can be rendered inaccurate for purposes of medical diagnoses. Common mode interference can be a type of interference that affects ECGs, among other electrophysiological measurements. In order to reduce and/or eliminate such interference, channels of the ECG, or other electrophysiological measurement systems, can be calibrated to identify filter parameters for individually mitigating common mode interference occurring at an ECG vector or voltage difference between groups of electrodes. Filters can be applied to electrode signals before voltage differences are calculated between electrodes. In some implementations, a degree of common mode interference removal can be measured as a ratio referred to as common mode rejection ratio (CMRR). The CMRR can be reduced to less than 1/10000 for an ECG, where a common mode signal of 1 Volt appears as an interference of 100 microvolts or less on an ECG wave.

According to some embodiments discussed herein, during calibration of the electrode channels, test signals can be supplied to the electrode channels. It should be noted that an electrode channel can refer to a single electrode of ECG device and an ECG channel can refer to an ECG vector or voltage difference between electrode channels. Each electrode channel can be connected to analog circuitry that can perform input related and/or output related functions for the electrode channel. For example, because the signals measured by an ECG can be relatively small, the input to an electrode channel can be connected to an amplifier that can amplify signals provided at the input of the electrode channel. Test signals provided to the electrode channels can cause response signals to be generated at the analog circuitry, and the response signals can be digitally sampled. The digitally sampled response signals can be synchronously recorded and used to calculate parameters for individual filters that can be applied to each electrode channel. For example, coefficient parameters can be derived from the recorded responses and used to create digital filters for the inputs of the electrode channels. The filters can be programmed to minimize time-domain differences between signals of each input channel and a desired response. Furthermore, as a result of applying the filters to each electrode channel, common mode interference signals can be more readily mitigated and/or canceled.

Coefficients for the filters can be derived based on one or more ECG calibrations where the electrodes and/or other frontend circuitry of the ECG system are in communication with a testing system that can provide test signals to the ECG system. In this arrangement, the electrodes can be configured as inputs for the test signals. The test signals can be sine waves, square waves, triangle waves, and/or any waves or superimposed combination of waves, such as a square wave superimposed with a sine wave, suitable for testing a circuit. For example, using a square wave that is superimposed with a sine wave can limit the number of solutions when deriving coefficients for the filters. Furthermore, because the response signals can be sampled at an output of an analog-to-digital converter (ADC), a frequency of the test signals can be selected according to a bandwidth of the ECG being tested. In this way, it can be ensured that any sample data provided through the test signals can be sampled at the ADC output.

In some embodiments, the analog circuitry can have a bandwidth of at least 1.5 kHz. Each electrode channel can be sampled with an ADC sampling rate of 32 kHz. The filters described herein can be applied at the same sampling rate as the ADC. Furthermore, the electrode channels can be downsampled at an 8 kHz sampling rate for further processing (e.g., ECG vector calculation, pacemaker pulse detection, electrode on/off detection, electrode impedance measurement). Additionally, low-pass and high-pass filters can be applied to limit the bandwidth to 0.05-150 Hz, and the sampling rate can be reduced to 500 Hz for output, display, heart rate calculation, and arrhythmia detection.

An ECG can include multiple channels, and samples of ADC output data can be collected for each channel. In other words, the response of each analog circuitry associated with each channel can be sampled and stored for purposes of deriving filter parameters from the sampled data. Response signals can be analyzed to identify which response signal is the slowest and/or has the largest delay out of all the response signals. For example, zero-line crossings and/or slew rate of the response signals can be analyzed to identify delays caused by the analog circuitry. Another source of delays can be sequential sampling of ADC channels. Such delays can occur if there are fewer ADCs than electrode channels and the electrodes are not all sampled at the same point in time (for example, in some embodiments, two ADCs can be employed to sample the analog circuitry, and each ADC can include a built-in multiplexer for sampling all electrode channels (e.g., 10 channels) in a sequence, which takes approximately 30 microseconds and is repeated continuously). The response signal that is the slowest or has the greatest delay can be selected as the signal to be reproduced by each filter. In other words, each filter can cause similar delays at other channels to reduce time-domain differences between the other channels and avoid side effects that can be associated time domain-differences, such as introducing higher frequency noise. In some embodiments, the response signal that is the fastest or has the smallest delay can be selected as the signal to be reproduced by each filter, in order to expedite the signals from the slower channels. Using samples of the selected response signal, coefficients can be calculated for filtering the other response signals associated with other channels to be more similar, and ideally identical, to the selected response signal. For example, the filter for each channel can be a digital finite impulse response (FIR) filter that operates according to one or more coefficients that are generated using the samples of the other response signals and the selected response signal. The samples can be arranged as part of an equation where each value from the selected response signal is set equal to a product of a coefficient and a number of samples from a response signal of a channel for which the coefficient is to be solved. This equation can be duplicated for a number of coefficients and response signal samples. The resulting equations can be solved using a least squares approach that minimizes the sum of the squared errors for each equation. As a result, a set of coefficients can be adapted for each channel for use as filter parameters for modifying signals from each of the channels. The coefficients can be stored by the ECG and used during normal operations for filtering electrophysiological signals and/or analog circuitry response signals. In some embodiments, an infinite impulse response filter can be used in combination with, or in place of, the finite impulse response filter.

Figure 1:
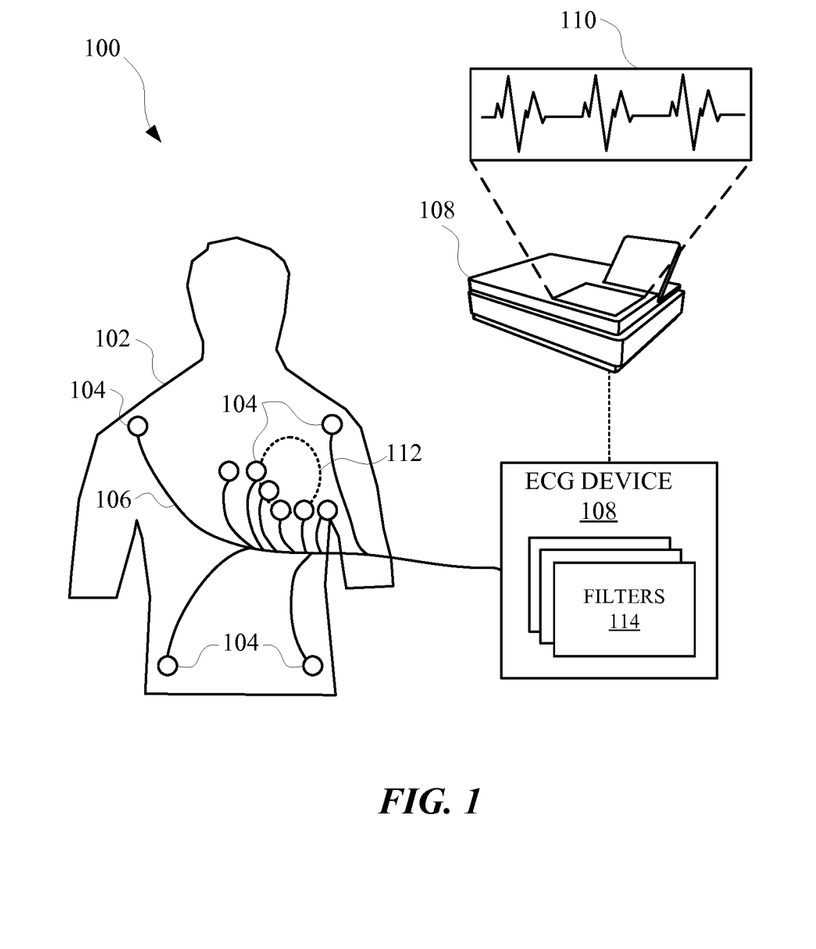
FIG. 1 illustrates a system diagram of an electrocardiogram (ECG) device that uses filters to improve signal quality when performing electrophysiological measurements on a person.

FIG. 1 illustrates a system diagram 100 of an ECG device 108 that uses one or more filters 114 to improve signal quality when performing electrophysiological measurements on a person 102. The ECG device 108 can include one or more cables 106 that provide a conductive pathway between electrodes 104 that are attached to the person 102 and the ECG device 108. The electrodes 104 can provide electrical potentials across the body of the person 102, and the electrical potentials can be affected by the changes in polarity of the heart 112. The placement of the electrodes 104 are selected in order to capture the changes in polarity at different angles that correspond to vectors between the electrodes 104. As the electrical potentials of the electrodes 104 are modified by the changes in polarity of the heart 112, the ECG device 108 can process the changes to the electrical potentials and generate a resulting signal 110 that represents the electrical activity associated with the heart 112. However, because the changes in polarity of the heart 112 modify the electrical potentials of the electrodes 104 only slightly at times, differentiating the changes in electrical potential from electrical interference can prove difficult. Electrical interference can take the form of common mode interference, which can result from external sources, such as electrical line interference, or internal sources such as capacitive coupling between portions of the ECG device 108. In order to mitigate and/or eliminate the interference, the ECG device 108 can include one or more hardware and/or software filters 114 for filtering the signals received at the electrodes 104. The filters 114 can operate according to parameters that can include coefficients, which can be derived during a calibration of the ECG device 108. Each electrode 104 can be assigned to a filter 114, and each coefficient for each electrode 104 can be provided to minimize time-domain differences and interference of signals from each electrode 104.

Figure 2:
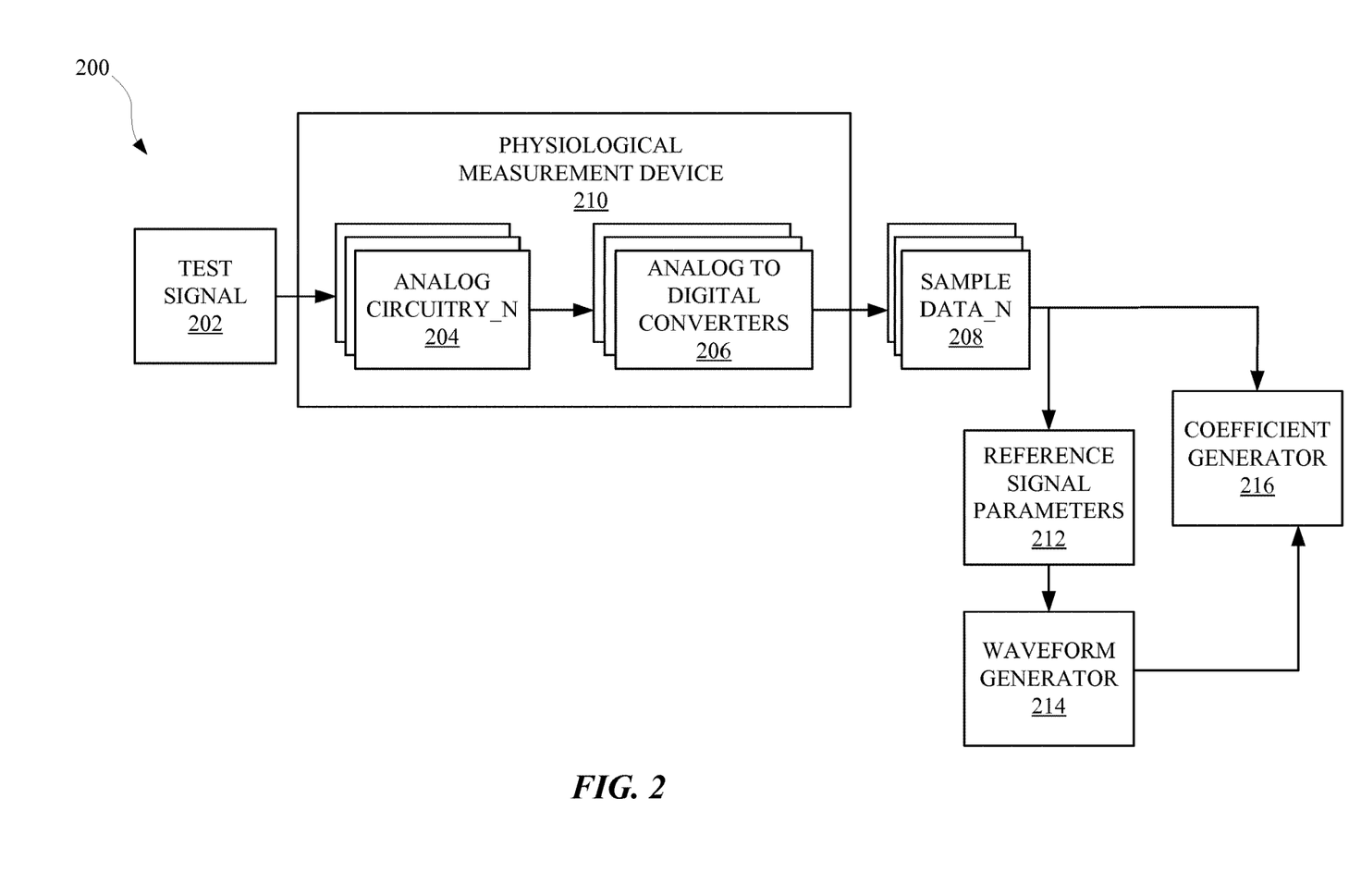
FIG. 2 illustrates a system for performing a calibration of a physiological measurement device, such as an ECG device, in order to generate coefficients for filters that can be applied during operation of the physiological measurement device.

FIG. 2 illustrates a system 200 for performing a calibration of a physiological measurement device 210, such as an ECG device, in order to generate coefficients for filters that can be applied during operation of the physiological measurement device. The system 200 can be embodied as software and/or hardware on one or more devices that are capable of interacting with a physiological measurement device. During calibration of a physiological measurement device 210, a test signal 202 can be provided to analog circuitry_N 204. The test signal 202 can be transmitted to electrodes that are connected to each of the analog circuitry_N 204. It should be noted that there can be any number of analog circuits, as indicated by "N", which can refer to any positive whole number greater than 1. The test signal 202 can be a sine wave, triangle wave, square wave, multiple superimposed waves, and/or any other wave suitable for calibrating a device. In some embodiments, the test signal 202 is a square wave that is superimposed with a sine wave that has a higher frequency than the square wave. In this way, by adding a higher frequency component, such as a sine wave, the number of solutions for coefficients can be limited. A frequency of the square wave can be less than a bandwidth of the physiological measurement device and the frequency of the sine wave can be less than half the frequency of the sample rate at which digital samples are taken from the analog circuitry_N 204. For example, the bandwidth for the physiological measurement device can be 150 Hertz (Hz), and the frequency for the square wave can be less than 150 Hz (e.g., 140 Hz). Furthermore, the sample rate can be 32 kHz, and the frequency for the sine wave that is superimposed with the square wave can be less than 16 kHz (e.g., 6 kHz). However, in some embodiments, analog circuitry with a higher edge frequency could be used with test signals that are outside of the ECG bandwidth but can still achieve sufficient gain matching inside the ECG bandwidth.

As the test signal 202 is provided to each analog circuitry_N 204, a response signal from each analog circuitry_N 204 can be sampled. The response signals can be sampled by analog to digital converters (ADCs) 206, respectively. In some embodiments, a single ADC is used, and the response signals from each channel can be transmitted to the ADC using a multiplexer attached between the ADC and the analog circuitry. In other embodiments, digital samples are captured by multiple ADCs 206 and stored in one or more memory devices for subsequent analysis.

Initially, the samples for each channel can be recorded as sample data_N 208. The recorded sample sets can then be analyzed by the system 200 to determine which analog circuitry_N 204 and/or input channel is associated with the slowest or most delayed response out of the all the analog circuitry_N 204 and/or input channels. The slowest or most delayed response signal can be selected by identifying the response signal that was the latest in time, had the slowest slew rate, and/or had the latest zero crossing compared to other response signals. Slew rate can correspond to a response rate for an electrical component, such as an amplifier. Therefore, the response signal with the slowest slew rate can have the smallest slope or gradient compared to other response signals that were provided by analog circuitry receiving some input. The samples corresponding to the selected response signal can then be designated as a source for reference signal parameters 212. By using the slowest or most delayed response signal as a source for the reference signal parameters 212, it can be ensured that the resulting filters will have low pass behavior, avoid causing unintended side effects from speeding up or shifting other response signals, and mitigate time-domain differences between input channels.

Once the reference signal parameters 212 have been derived from the samples of the selected response signal corresponding to the slowest or most delayed channel, the reference signal parameters 212 are supplied to a waveform generator 214 of the system 200. The waveform generator 214 can use the reference signal parameters 212 to construct the selected response signal that was transmitted by the slowest or most delayed analog circuitry and/or input channel. The reconstructed response signal can then be supplied to a coefficient generator 216. The coefficient generator 216 can calculate coefficients that can be used by filters that, when applied to the sample data_N 208, result in a signal that is more similar, and ideally identical, to the selected response signal.

The coefficients can be generated by the coefficient generator 216 using a set of equations that equate samples of the response signals from each channel to values of the reconstructed selected response signal. For example, the set of equations can be linear equations with multiple coefficients that can be solved or estimated in order to generate a set of coefficients that will accurately convert the samples into values of the selected response signal. Differences between the reconstructed signal and the selected response signal can be minimized through this method by repeatedly estimating solutions to the equations to minimize error. For example, minimizing error can be performed by a least means square algorithm, a recursive least squares algorithm, and/or any other algorithm for producing a solution with minimal error.

Equation (1) illustrates a set of matrices that can be solved in order to derive coefficients for the filters. In Equation (1), values for can correspond to sampled values from a response signal of the analog circuitry_N 204, values for can correspond to the selected response signal (e.g., the slowest or most delayed response signal) from which the coefficients are based, and values for can correspond to the coefficient values. There can be any number of coefficients (e.g., there can be coefficients where is any real number greater than 1), and the coefficients can be solved using the set of linear equations established by Equation (1). Although there may not be an exact solution for a finite number of coefficients, the Equation (1) can be solved using one or more error minimizing algorithms. Furthermore, any number of samples can be used, wherein and are any real numbers greater than 0.

$$\begin{bmatrix} x_n & x_{n-1} & x_{n-2} & x_{n-3} & x_{n-4} \\ x_{n+1} & x_n & x_{n-1} & x_{n-2} & x_{n-3} \\ \ldots & \ldots & \ldots & \ldots & \ldots \\ x_m & x_{m-1} & x_{m-2} & x_{m-3} & x_{m-4} \end{bmatrix} \begin{bmatrix} a_1 \\ a_2 \\ \ldots \\ a_z \end{bmatrix} = \begin{bmatrix} y(n) \\ y(n+1) \\ \ldots \\ y(m) \end{bmatrix} \qquad \text{Eq. (1)}$$

Once the coefficients have been derived for each input channel of analog circuitry_N 204, the coefficients can be stored in a non-volatile memory that is accessible by the physiological measurement device 210. The coefficients can then be used by the physiological measurement device 210 to control filters for filtering response signals at the physiological measurement device 210. The filters can be finite impulse response filters and/or infinite impulse response filters. Furthermore, in some embodiments, the reconstructed selected response signal can be modified in amplitude and/or frequency compared to the selected response signal, in order to further filter any noise or interference that can occur at the channels.

Figure 3:
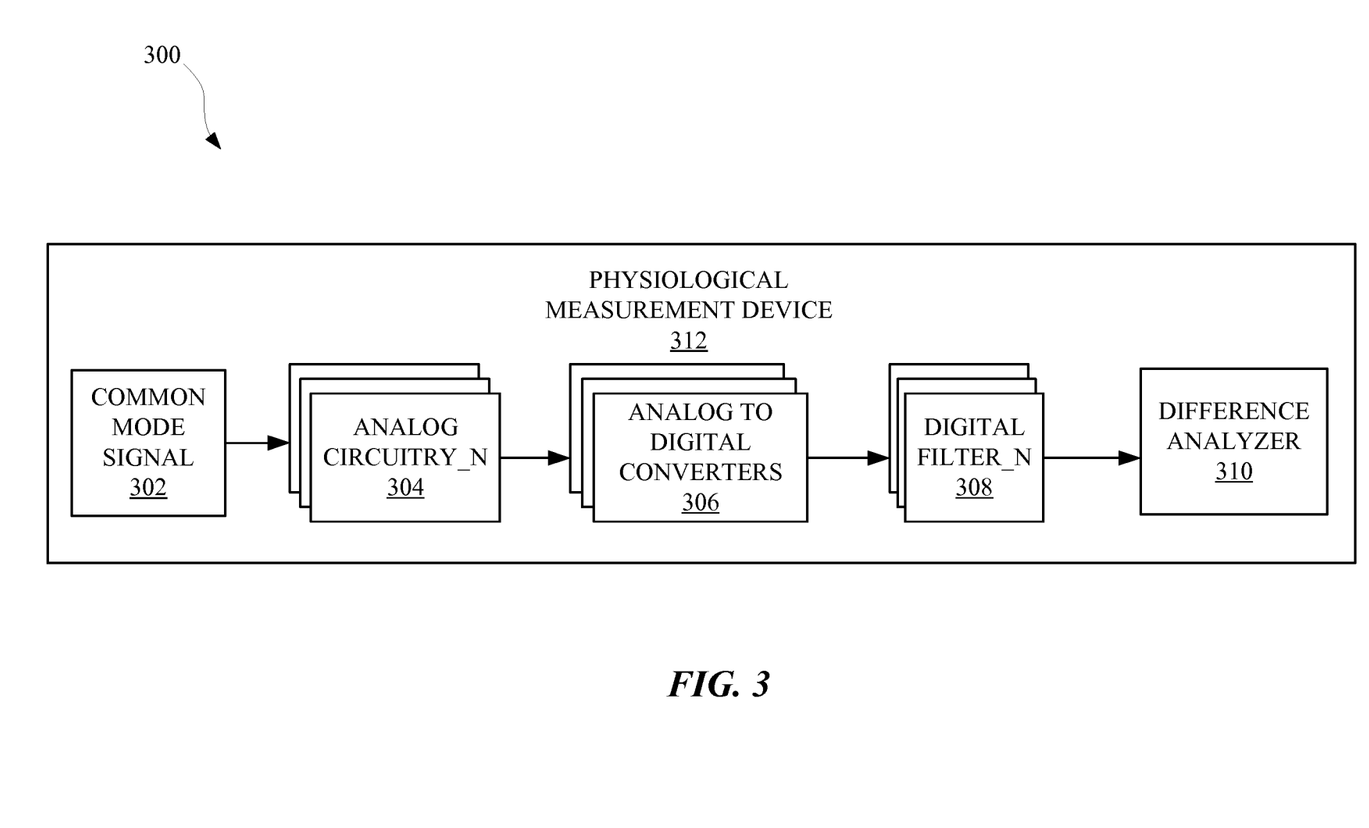
FIG. 3 illustrates a system for applying individual filters to separate channels of a physiological measurement device.

FIG. 3 illustrates a system 300 for applying individual filters to separate channels of a physiological measurement device 312. The system 300 can be embodied as hardware and/or software one or more devices capable of interacting with the physiological measurement device 312. The system 300 can generate a common mode signal 302 that is transmitted to electrodes that are connected to analog circuitry_N 304, where N is any positive whole number, equal or greater than 2, that represents the number of analog circuits and/or electrode channels. The common mode signal 302 can be affected by interference that can occur external to a body of a person to which the electrodes are attached, and the interference can be detected by analog circuitry_N 304. Each of the analog circuitry_N 304 can exhibit a response signal to the changes to the common mode signal 302. Response signals from analog circuitry_N 304, which can correspond to individual electrode channels, can be converted into digital signals at one or more digital filters_N 308.

Each digital filter_N 308 can operate based at least on a coefficient parameter that can effectively mitigate time-domain differences between response signals traveling across each channel. By mitigating time domain differences between response signals, common mode interference can be canceled out when a difference analyzer 310 of the physiological measurement device 312 calculates differential signals between channels. The resulting differential signals can correspond to vector waves that can be provided to a monitor for visualizing physiological measurements.

Figure 4:
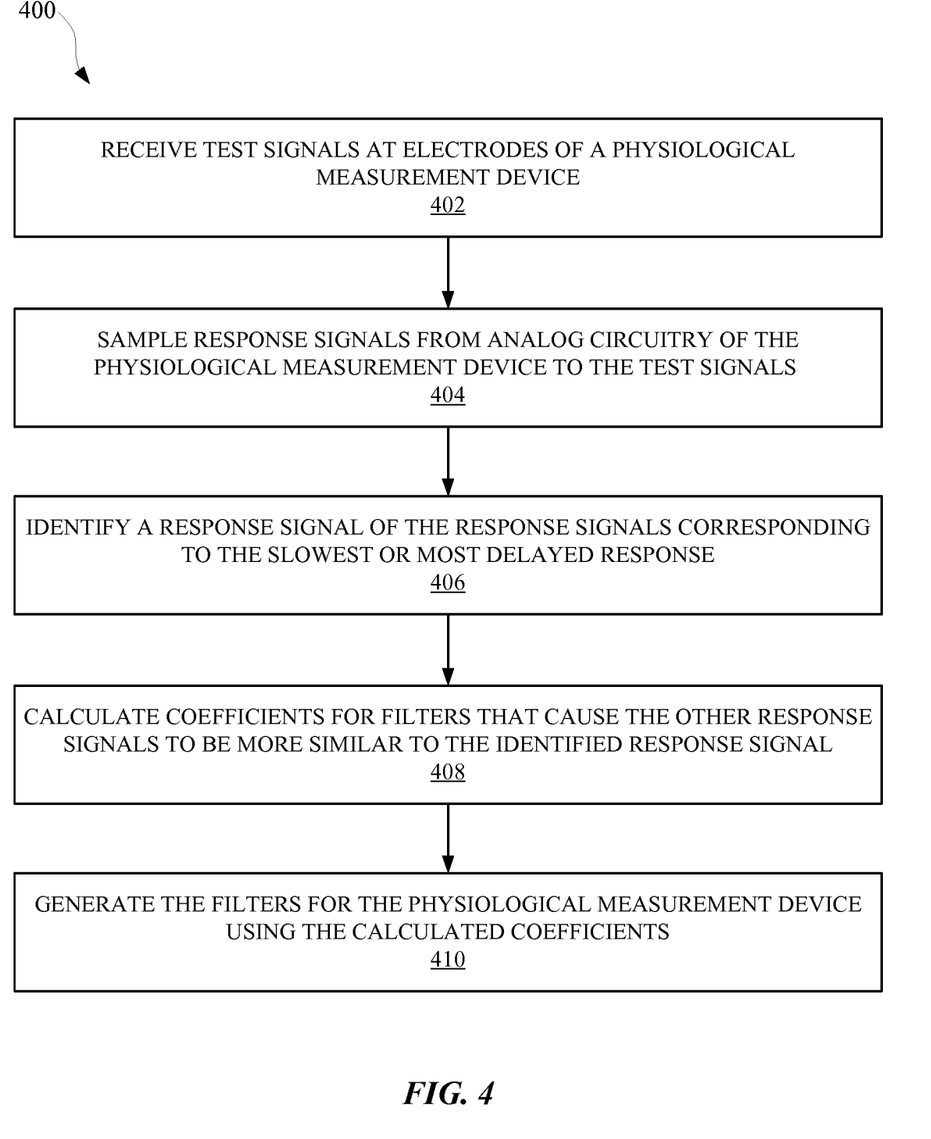
FIG. 4 illustrates a method for creating filters for channels of a physiological measurement device.

FIG. 4 illustrates a method 400 for creating filters for channels of a physiological measurement device. The method 400 can be performed by any computing device, physiological measurement device, medical device, calibration device, and/or any apparatus suitable for calculating parameters for one or more filters. The method 400 can include a block 402 of receiving test signals at electrodes of a physiological measurement device. Each electrode of the physiological measurement device can correspond to a channel that can include analog circuitry for receiving the test signal. For example, the physiological measurement device can be an electrocardiogram (ECG) device that includes multiple wires with electrodes at distal ends of the wires for attaching to a person for monitoring a rhythm of the person's heart. The method 400 can further a block 404 of sampling response signals from analog circuitry of the physiological measurement device to the test signals. In some embodiments, the response signals are converted to digital signals before being sampled. The conversion to digital signals can be performed by one or more analog to digital converters. For example, a single analog to digital can be connected in series with a multiplexer that switches between connections to the analog circuitry in order to create a time series of digital samples from the analog circuitry. The sampled response signals can be stored in memory in association with each channel from which they were originally transmitted. In this way, coefficients derived from the processing of the samples can later be stored in association with the same channels.

The method 400 can further include a block 406 of identifying a response signal of the response signals that corresponds to the slowest or most delayed response. Identifying the response signal corresponding to the slowest or most delayed response can include identifying the response signal that has the slowest slew rate, crosses zero sooner than other response signals, and/or includes any other feature that indicates the response signal is the result of a slower response than other response signals. The method 400 can also include a block 408 of calculating coefficients for filters that can cause the other response signals to be more similar to the identified response signal. The coefficients can be calculated using samples of the other response signals and the identified response signal. Samples of the identified response signal can be set equal to a product of at least one set of samples of one of the other response signals and a set of coefficients. The coefficients can be solved for using a least squares method for calculating the coefficients, and/or any other method for solving for coefficients from sets of values. At block 410, the filters for the physiological measurement device can be generated using at least the calculated coefficients. The filters can be finite impulse response filters that act to mitigate time domain differences of response signals at each channel of the physiological measurement device. In this way, when the physiological measurement device generates differential signals from the response signals from each channel, any common mode interference can be canceled out to reveal a more refined signal representative of the physiological measurement being undertaken.

Figure 5:
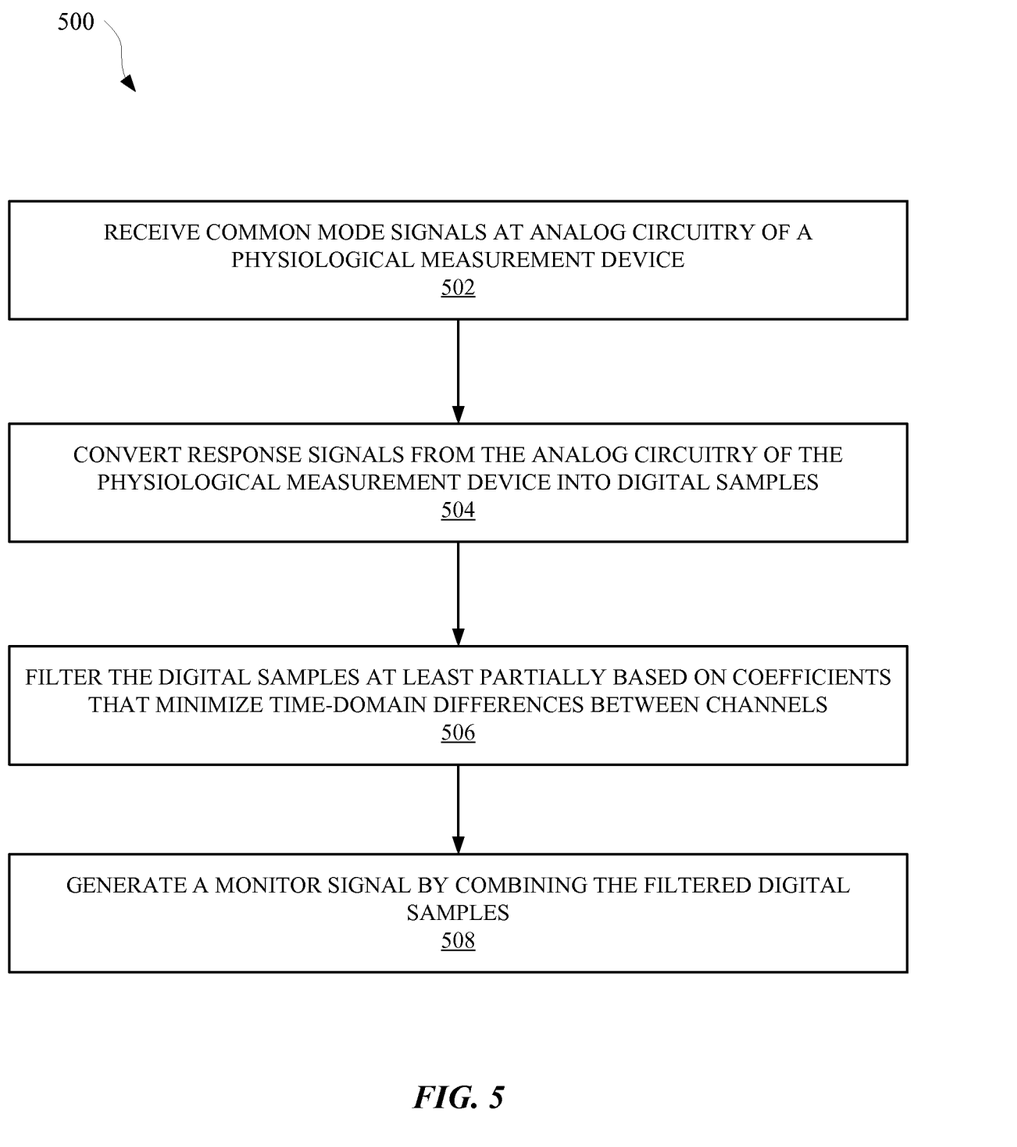
FIG. 5 illustrates a method for generating a filtered monitor signal at a physiological measurement device.

FIG. 5 illustrates a method 500 for generating a filtered monitor signal at a physiological measurement device. The method 500 can be performed by any computing device, physiological measurement device, medical device, calibration device, and/or any apparatus suitable for employing a filter to generate a signal. The method 500 can include a block 502 of receiving common mode signals at analog circuitry of a physiological measurement device. The common mode signals can be one or more voltages received at electrodes attached to a person for monitoring a physiological condition of the person, and the electrodes can be in communication with the analog circuitry. The method 500 can further include a block 504 of converting response signals from the analog circuitry of the physiological measurement device into digital samples. The response signals can be converted into digital samples using one or more digital converters that sample response signals from analog circuitry associated with different channels of the physiological measurement device. The method 500 can also include a block 506 of filtering the digital samples at least partially based on coefficients that minimize time-domain differences between channels. By minimizing time-domain differences between channels and response signals from the channels, subsequent differential signals made from the response signals can more accurately model the physiological features they are intended to represent. At block 508, a monitor signal is generated by combining the filtered digital samples. Combining the filtered digital samples can include taking a difference between the filtered digital samples derived from the response signals of each channel.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases. It should be understood that certain expressions and reference signs used in the claims do not limit the scope.

The invention claimed is:

1. A method for minimizing common mode interference in a physiological measurement system having input channels and analog circuitry electrically coupled to electrodes for measuring an electrophysiological signal, the method comprising:
   receiving analog test signals at the input channels;
   generating response signals at the analog circuitry in response to receiving the analog test signals;
   converting each response signal into digital data samples;
   storing, in a memory of the physiological measurement system, the digital data samples in association with each of the input channels;
   analyzing the digital data samples for each of the input channels to determine a reference input channel;
   determining a set of digital filter coefficients for each input channel other than the reference input channel; and
   applying a filter to each input channel during operation of said physiological measurement system, wherein each filter operates according to a digital filter coefficient from the set of digital filter coefficients to minimize time-domain differences between the reference input channel and each input channel other than the reference input channel, wherein analyzing the digital data samples for each of the input channels to determine the reference input channel comprises one of:
   identifying a response signal corresponding to a last zero crossing; and
   identifying a response signal corresponding to a slowest slew rate.

2. The method of claim 1, wherein the analog test signals include a square wave that is superimposed with a sine wave.

3. The method of claim 2, wherein converting each response signal into digital samples includes sampling at least one response signal at a rate that is greater than a frequency of the sine wave.

4. The method of claim 2, wherein the square wave has a frequency that is less than a bandwidth of the physiological measurement system.

5. The method of claim 1, wherein the set of digital filter coefficients are calculated according to a least squares error estimation.

6. The method of claim 1, wherein the filter at each input channel is a finite impulse response filter.

7. The method of claim 6, wherein the set of digital filter coefficients comprises at least 2 coefficients.

8. The method of claim 1, wherein converting each response signal into digital data samples is performed using sequential data sampling with an analog to digital converter and a multiplexer that is connected between the analog to digital converter and the analog circuitry.

9. The method of claim 8, wherein the sequential data sampling is performed at least at 32000 samples per second.

* * * * *